US010525157B2

United States Patent
Fu et al.

(10) Patent No.: US 10,525,157 B2
(45) Date of Patent: Jan. 7, 2020

(54) ALUMINUM-COMPATIBLE COMPOSITIONS FOR 2-PART ALKALINE DISINFECTANTS AND SANITIZERS

(71) Applicant: Sterilex LLC, Hunt Valley, MD (US)

(72) Inventors: Edward Fu, Hunt Valley, MD (US); Mark Wozniak, Hunt Valley, MD (US); Chris Bergstrom, Hunt Valley, MD (US)

(73) Assignee: Sterilex, LLC, Hunt Valley, MD (US)

( * ) Notice: Subject to any disclaimer, the term of this patent is extended or adjusted under 35 U.S.C. 154(b) by 0 days.

(21) Appl. No.: 15/664,122

(22) Filed: Jul. 31, 2017

(65) Prior Publication Data

US 2018/0028701 A1 Feb. 1, 2018

Related U.S. Application Data

(60) Provisional application No. 62/369,176, filed on Jul. 31, 2016.

(51) Int. Cl.
| | | |
|---|---|---|
| *A61L 2/18* | (2006.01) | |
| *A01N 33/12* | (2006.01) | |
| *A01N 59/00* | (2006.01) | |
| *A23L 3/3454* | (2006.01) | |
| *A61L 2/22* | (2006.01) | |
| *A61L 2/235* | (2006.01) | |

(52) U.S. Cl.
CPC .............. *A61L 2/186* (2013.01); *A01N 33/12* (2013.01); *A01N 59/00* (2013.01); *A23L 3/3454* (2013.01); *A61L 2/22* (2013.01); *A61L 2/235* (2013.01); *A23V 2002/00* (2013.01)

(58) Field of Classification Search
CPC ....... A01N 33/12; A01N 59/00; A23L 3/3454; A61L 2/18; A61L 2/186; A23V 2002/00
See application file for complete search history.

(56) References Cited

U.S. PATENT DOCUMENTS

| | | | | |
|---|---|---|---|---|
| 5,242,621 A | * | 9/1993 | Miller | C09K 5/20 252/389.61 |
| 2012/0111743 A1 | * | 5/2012 | Kramer | C11D 1/62 206/219 |
| 2016/0074549 A1 | * | 3/2016 | Lei | A01N 59/00 424/616 |

FOREIGN PATENT DOCUMENTS

| | | |
|---|---|---|
| DE | 10 2007 000501 A1 | 4/2009 |
| EP | 1 237 664 B1 | 7/2005 |
| WO | WO 97/11151 A1 | 3/1997 |
| WO | WO 2016/044607 A1 | 3/2016 |

OTHER PUBLICATIONS

PH of common acids and bases 2016 (http://www.aqion.de/site/191).*
International Search Report and Written Opinion dated Sep. 27, 2017 for Application No. PCT/US2017/044616, 10 pgs.

* cited by examiner

*Primary Examiner* — Blessing M Fubara
(74) *Attorney, Agent, or Firm* — Frost Brown Todd LLC (57) ABSTRACT

Alkaline in-use solutions that may be used to disinfect and/or sanitize hard surfaces and which may act as anti-biofilm agents, comprise a disinfectant/sanitizer cleaner solution and an activator solution that are mixed together to form the alkaline in-use solutions. Disinfectant/sanitizer cleaner solution may comprise quaternary ammonium compound and hydrogen peroxide. Activator solution may comprise alkaline buffering agent, chelating agent and soluble silicon dioxide.

12 Claims, 3 Drawing Sheets

ALUMINUM-COMPATIBLE COMPOSITIONS FOR 2-PART ALKALINE DISINFECTANTS AND SANITIZERS

PRIORITY

This application claims priority to U.S. Provisional Patent Application Ser. No. 62/369,176, filed on Jul. 31, 2017, and entitled, "Aluminum-compatible compositions for 2-part alkaline disinfectants and sanitizers," the disclosure of which is incorporated herein.

TECHNICAL FIELD

The present disclosure is directed to 2-part alkaline disinfectant and/or sanitizer solutions that are: safe for use on aluminum and other soft (easily-corroded) metal surfaces, and safe for use on plastic surfaces. The 2-part alkaline disinfectant and/or sanitizer solutions are useful on food contact surfaces in food handling and processing such as in grocery, dairy, restaurant and food service applications. The 2-part alkaline disinfectant and/or sanitizer solutions are especially useful on food contact surfaces in food and dairy processing.

The 2-part alkaline disinfectant and/or sanitizer solutions may also act as anti-biofilm agents.

BACKGROUND

Alkaline disinfectant and/or sanitizer solutions, are known. Effective alkaline disinfectant and/or sanitizer solutions may be especially useful in food handling and processing such as in grocery, dairy, restaurant and food service applications, where surfaces (e.g., equipment) may be vulnerable to problems with biofilm formation due to the prevalence of microbial food sources. The 2-part alkaline disinfectant and/or sanitizer solutions are especially useful on food contact surfaces in food and dairy processing.

In some instances, it is useful to activate a disinfectant/sanitizer cleaner solution via addition of an activator solution to produce an activated (i.e. "in-use") disinfectant and/or sanitizer solution at or near a substrate to be treated. By combining a disinfectant/sanitizer cleaner solution with an activator solution at or near the substrate to be treated, efficacy of the resulting activated disinfectant and/or sanitizer solution may be increased, for example by keeping incompatible compounds separate until time of use. An example of one such "2-part system," is a system comprising Ultra Disinfectant Cleaner Solution 1 and Ultra Activator Solution, each from Sterilex® (Hunt Valley, Md.). In use, Sterilex® Ultra Disinfectant Cleaner Solution 1 and Sterilex® Ultra Activator Solution may be mixed together in equal volumes and diluted with water to create an alkaline in-use disinfectant and/or sanitizer solution. The alkaline in-use disinfectant and/or sanitizer solution may be applied to a substrate to be treated using any suitable method including, but not limited to, being applied as a foam or spray, used as soaking solution and/or circulated through or around a substrate.

One industrial area in which 2-part systems may be particularly useful, is to treat heat exchanger coils which can be found in spiral freezers and other freezing/chilling equipment used for processing frozen foods. Additional industrial areas in which 2-part systems may be particularly useful include overhead air handling units, cooling tunnels, aluminum paneling and walls. However, these and other substrates may comprise components that may be vulnerable to corrosive effects of compounds commonly found in alkaline in-use disinfectant and/or sanitizer solutions. For example, aluminum, which is a soft metal, is commonly used as a component of coils in spiral freezers and other equipment. However, aluminum is prone to rapid corrosion upon contact with alkaline substances.

While various 2-part alkaline disinfectant and/or sanitizer solutions have been made and used, it is believed that no one prior to the inventor(s) has made or used the invention described in the appended claims, which reduce or eliminate the corrosive effects of alkaline disinfectant and/or sanitizer solutions.

BRIEF DESCRIPTION OF THE DRAWINGS

The accompanying drawings incorporated in and forming a part of the specification illustrates several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

It has been discovered that it is possible to mitigate corrosion of substrates to be treated with 2-part alkaline disinfectant and/or sanitizer solutions by adding metasilicate to an activator solution that is then combined with a disinfectant/sanitizer cleaner solution to make alkaline in-use disinfectant and/or sanitizer solutions. Thus, 2-part alkaline disinfectant and/or sanitizer solutions according to the present disclosure may allow for treatment of substrates including exchanger coils, that are found for example, in spiral freezers.

"Disinfectant" as used herein refers to a substance or a mixture of substances (including solutions) that destroy or irreversibly inactivate bacteria, fungi and viruses, but not necessarily bacterial spores, in an inanimate environment or on a surface (e.g., in or on a substrate).

"Sanitizer" as used as used herein refers to a substance or a mixture of substances (including solutions) that reduce a bacterial population in an inanimate environment (e.g., a substrate) by significant numbers, (e.g., a 3 log 10 reduction) or more, but that does not destroy or eliminate all bacteria.

It should be noted that alkaline in-use solutions as described herein may act as a disinfectant and a sanitizer by respectively destroying or irreversibly inactivating certain bacteria, fungi and/or viruses present on a substrate, and reducing the population of certain other bacteria that are present on the same substrate. For this reason, general descriptions herein of in-use solutions refer to in-use solutions as "disinfectant and/or sanitizer solutions."

It should also be noted that alkaline in-use solutions as described herein remove biofilm from various substrates in addition to, or in alternative to, acting as a disinfectant and/or sanitizer. Thus, alkaline in-use solutions act as a "biofilm removal agent."

"Soft metals" as described herein mean metals that are susceptible to corrosion by alkaline disinfectant and/or sanitizer solutions. Exemplary soft metals may be selected from the group of: aluminum (e.g., aluminum 1100, 3003, 7075 and 5052), copper and brass.

The terms "2-part alkaline disinfectant and/or sanitizer solutions," "alkaline disinfectant and/or sanitizer solutions," "alkaline in-use solutions" and "alkaline disinfectant and/or sanitizer" are used interchangeably herein.

Exemplary 2-part alkaline disinfectants and/or sanitizer solutions that may be modified per the present disclosure to mitigate or eliminate their corrosive effects, may comprise disinfectant/sanitizer cleaner solution and activator solution.

Disinfectant/Sanitizer Cleaner Solution:

Disinfectant/sanitizer cleaner solutions comprise quaternary ammonium compound, hydrogen peroxide, water, and in some exemplary disinfectant/sanitizer cleaner solutions, adjunct ingredients.

Quaternary ammonium compounds ("QACs"), may act as antimicrobial agents and may be present in a disinfectant/sanitizer cleaner solution at a weight percentage of the solution of from about 0.5% to about 10%, from about 1% to about 9%, from about 4% to about 8% or from about 5% to about 7%. Useful commercially available QACs may be present in an aqueous solution, which is then added to other components in exemplary disinfectant/sanitizer cleaner solutions.

Exemplary QACs generally have the following formula $R_1R_2R_3R_4N^+X^-$. Depending on the nature of the R groups, the anion, and the number of quaternary nitrogen atoms present, the antimicrobial QACs are typically classified as mono alkyl trimethyl ammonium compounds, mono alkyl dimethyl benzyl ammonium salts, dialkyl dimethyl ammonium salts, heteroaromatic ammonium salts, polysubstituted quaternary ammonium salts, bisquaternary ammonium salts or polymeric ammonium salts. Examples of mono alkyl trimethyl ammonium salts include cetyl trimethyl ammonium bromide (CTAB); alkyl trimethyl ammonium chloride; alkyl aryl trimethyl ammonium chloride; cetyl dimethyl ethyl ammonium bromide. Examples of mono alkyl dimethyl benzyl ammonium salts include alkyl dimethyl benzyl ammonium chlorides; dodecyl dimethyl 3,4 dichlorobenzyl ammonium chloride; and mixtures of alkyl dimethyl benzyl and alkyl dimethyl substituted benzyl(ethyl benzyl) ammonium chlorides. Examples of dialkyl dimethyl ammonium salts include didecyl dimethyl ammonium halides and octyl dodoceyl dimethyl ammonium chlorides. Examples of heteroaromatic ammonium salts include cetylpyridinium halide (CPC); 1-[3-chloroallyl]-3,5,7-triaza-1-azoniaadamantane; alkyl-isoquinoliniumm bromide and alkyldimethylnaphthylmethyl ammonium chloride. Examples of polysubstituted quaternary ammonium compounds include alkyl dimethyl benzyl ammonium saccharinate and alkyl dimethylethylbenzyl ammonium cycloheylsulfamate. Examples of bis-quatemary ammonium salts include 1,10-bis (2-mthyl-4-aminoquinolinium chloride)-decane; b1,6-Bis [1-methyl-3-(2,2,6-trmethyl cyclohexyl)-propyldimethyl ammonium chloride] hexane.

In some exemplary disinfectant/sanitizer cleaner solutions, suitable quaternary ammonium compounds may be selected from the group of: alkyl dimethyl benzyl ammonium chlorides, alkyl dimethyl ethyl benzyl ammonium chlorides, dialkyl dimethyl quaternary compounds and combinations thereof.

Alkyl dimethyl benzyl ammonium chlorides of use may have an alkyl group which is a mixture of about 50% C14, 40% C12 and 10% C16. Another alkyl dimethyl benzyl ammonium chloride of use has an alkyl group which is a mixture of about 5% C12, 60% C14, 30% C16 and 5% C18.

Alkyl dimethyl ethyl benzyl ammonium chlorides of use in the invention may include those where the distribution of alkyl groups are about as follows: 50% C12, 30% C14, 17% C16 and 3% C18. Another group of quaternary ammonium compound of use are alkyl dimethyl ethyl benzyl ammonium chlorides wherein the alkyl group has the distribution of about 68% C12 and about 32% C14.

Dialkyl dimethyl ammonium chlorides of use may include didecyl dimethyl ammonium chlorides; dioctyl dimethyl ammonium chloride; didecyl dimethyl ammonium chloride and octyl dodecyl dimethyl ammonium chloride.

Mixtures of the quaternary ammonium compounds would also be of use per the present disclosure.

Hydrogen peroxide may be present in a disinfectant solution at a weight percentage of the solution of from about 0.5% to about 10%, from about 1% to about 9%, from about 4% to about 8% or from about 5% to about 7%.

Adjunct ingredients may be present in a disinfectant/sanitizer cleaner solution at any useful weight percentage of the disinfectant solution. Adjunct ingredients may be selected from the group of: dyes (e.g. fluorescent dyes including, but not limited to fluorescein), colorants, antifoam agents, foaming agents, thickening agents, surfactants and combinations thereof.

Once desired components of the disinfectant/sanitizer cleaner solution are mixed together, a sufficient quantity of water is added to the bring the solution up to the desired volume.

Some exemplary disinfectant/sanitizer cleaner solutions are made by mixing a powder with water prior to use. For example, a disinfectant/sanitizer powder comprising quaternary ammonium compound and a hydrogen peroxide source, e.g., sodium percarbonate, may be provided. Prior to use, it may be mixed with water to form a disinfectant/sanitizer cleaner solution.

A disinfectant/sanitizer cleaner solution may have any useful pH. Exemplary disinfectant/sanitizer cleaner solution may have a pH ranging from about 3 to about 6, from about 4 to about 6 or from about 5 to about 6.

An example of known disinfectant/sanitizer cleaner solution is Ultra Disinfectant Cleaner Solution 1 from Sterilex® (Hunt Valley, Md.).

Known Activator Solution:

Known activator solutions are combined with disinfectant/sanitizer cleaner solutions disclosed herein to make alkaline in-use disinfectant and/or sanitizer solutions. To enhance biofilm removal and disinfectant efficacy of alkaline in-use disinfectant and/or sanitizer solutions, known activator solutions may contain alkaline buffering agents, such as sodium and/or potassium carbonate and/or sodium and/or potassium bicarbonate, within a useful range of concentrations. Alkaline buffering agents may not be included in disinfectant/sanitizer cleaner solutions such as those described herein when they are manufactured or packaged, because when present with hydrogen peroxide in solution, storage stability issues may arise. Moreover, disinfectant/sanitizer cleaner solutions may be more effective in "soft" water (i.e. absent, e.g. calcium). Higher levels of calcium may also cause precipitation with alkaline buffering agents. For the foregoing reasons, known activator solutions may comprise alkaline buffering agent, chelating agent and water. Known activator solutions may comprise by weight percentage of the activator solution, from about 6% to about 16% of carbonate salts, from about 3% to about 8% ethylenediaminetetraacetic acid ("EDTA"), and the balance being water. An example of known activator solution is Ultra Activator Solution from Sterilex® (Hunt Valley, Md.).

Alkaline in-use Disinfectant and/or Sanitizer Solution:

Alkaline in-use solutions as described herein comprise disinfectant/sanitizer cleaner solution and activator solution. One skilled in the art may adjust the ratio of disinfectant/sanitizer cleaner solution to activator solution, and/or may add water to dilute a mixture of disinfectant/sanitizer cleaner solution and activator solution to obtain an alkaline in-use solution that acts as disinfectant, sanitizer and combinations thereof, noting that the resulting in-use solutions may also act as biofilm removal agent. An exemplary alkaline in-use disinfectant and/or sanitizer solution may comprise disinfectant/sanitizer cleaner solution and activator solution mixed together in a ratio of about 1:1. Some alkaline in-use solutions that act as a disinfectant and/or sanitizer may comprise a volume ratio of disinfectant/sanitizer cleaner solution to activator solution to water of from about 1:1:0 to about 1:1:128 and any combination of volume ratios in between. Some exemplary alkaline in-use solutions that are to be used to disinfect a substrate, may comprise in a volume ratio of disinfectant/sanitizer cleaner solution to activator solution to water of from about 1:1:0 to about 1:1:20, from about 1:1:1 to about 1:1:15 or from about 1:1:2 to about 1:1:10. Some exemplary alkaline in-use solutions that are to be used to sanitize a substrate, may comprise in a volume ratio of disinfectant/sanitizer cleaner solution to activator solution to water of from about 1:1:64 to about 1:1:128, from about 1:1:64 to about 1:1:100 or from about 1:1:70 to about 1:1:90.

Exemplary alkaline in-use disinfectant and/or sanitizer solutions may have a pH ranging from about 9 to about 13, or from about 10 to about 12.5.

A method of disinfecting or sanitizing a substrate comprises the steps of forming an alkaline in-use disinfectant and/or sanitizer solution by combining the disinfectant/sanitizer cleaner solution with an activator solution and applying the alkaline in-use disinfectant and/or sanitizer solution to a substrate. "Applying" as referred to herein includes, but is not limited to, being applied as a spray or foam, used as a soaking solution and/or circulated through or around the substrate. To disinfect the substrate, the method comprises leaving wet alkaline in-use disinfectant and/or sanitizer solution in contact with the surface of the substrate for about 3 minutes for sanitization and/or for about 10 minutes for disinfection.

A number of undesirable effects may arise when utilizing in-use disinfectant and/or sanitizer solutions that are alkaline. For example, alkaline in-use disinfectant and/or sanitizer solutions may be corrosive, particularly corrosive to soft metals, and more particularly, to aluminum. 2-part alkaline disinfectant and/or sterilizer solutions according to the present disclosure surprisingly overcome this issue through use of anti-corrosives as described below.

Anti-corrosives, for example silicates, are known. However, until now, adding silicates to 2-part alkaline disinfectant and/or sterilizer solutions has been problematic. For example, those of skill in the art would anticipate that addition of silicate to a disinfectant/sanitizer cleaner solution may negatively impact stability of hydrogen peroxide and quaternary ammonium present in the solution, thus reducing its shelf-life. Moreover, since disinfectant/sanitizer cleaner solution has an acidic pH, one of skill in the art would expect the silicate to be unstable, further reducing the shelf-life of the disinfectant/sanitizer cleaner solution.

If anti-corrosives, for example silicates, are instead added to activator solution, one of skill in the art would anticipate issues with solubility of the silicates, since the activator solution comprises relatively high levels of dissolved buffering and chelating agents.

In addition to the foregoing issues, one of skill in the art would anticipate that similar, if not the same issues with anti-corrosives, e.g., silicates, may occur once the disinfectant/sanitizer cleaner solution and activator solution are combined to produce an alkaline in-use disinfectant and/or sanitizer solution. Additional foreseeable issues include, but not limited to, the following.

First, an anti-corrosive should maintain solubility and effectiveness upon mixing of the 2-part system, and dilution of the resulting alkaline in-use disinfectant and/or sanitizer solution with water, especially hard water.

Second, an anti-corrosive may adversely impact the efficacy of the active ingredients in the alkaline in-use disinfectant and/or sanitizer solution that are required to achieve sanitization and disinfection claims per U.S. EPA regulations, as well as to maintain biofilm removal capabilities of thereof.

Third, it may be highly desirable for an alkaline in-use disinfectant and/or sanitizer solution to meet requirements for being useable in food processing plants. In other words, it may be desirable for an anticorrosive to be characterized by an acceptable toxicological and environmental profile, and preferably to have a Generally Recognized as Safe (GRAS) status with U.S. FDA in order to allow for use as a no-rinse sanitizer on food contact surfaces, and additionally or alternatively to also be free from restrictions relating to waste water release.

Based on the numerous restrictive requirements, identification of an effective anti-corrosive is not obvious to one of skill in the art. Chromates, phosphates, nitrates, silicates, and various organic compounds are known to have corrosion inhibiting properties. However, chromates, phosphates and nitrates do not have a GRAS status with the U.S. FDA, and are subject to restrictions relating to release in waste water. Thus, it would be desirable to utilize silicates, which do have the GRAS status as anticorrosives and are not subject to restrictions relating to release in waste water. However, one of skill in the art would recognize that silicates are sufficiently water soluble only at an alkaline pH, thus limiting the addition of silicates to the activator solution, which has an alkaline pH, rather than including the silicates in a disinfectant/sanitizer cleaner solution, which has an acidic pH. Mixing the resulting activator solution with disinfectant/sanitizer cleaner solution, may reduce the alkalinity required for silicate solubility in diluted alkaline in-use disinfectant and/or sanitizer solutions.

"Anti-Corrosive" Activator Solution:

Despite the foregoing, the inventors have surprisingly found new inexpensive activator solutions (e.g., due at least in part to a minimized number of additives) that may advantageously result in retention of some or all anticorrosive qualities of silicates, that may allow for silicate solubility in a number of diluted in use disinfectant and/or sanitizer solutions, that will have an approved status as U.S. FDA GRAS ingredient and/or that will not be subject to restrictions regarding its release in waste water, while unforeseeably achieving stable solutions. The resulting "anti-corrosive" activator solutions may be used in lieu of known activator solutions to make alkaline in-use disinfectant and/or sanitizer solutions as described above. The resulting anti-corrosive activator solutions may be substituted for known activator solutions in methods, including those described above, of disinfecting and/or sanitizing a substrate. The resulting alkaline in-use disinfectant and/or sanitizer solutions may be as effective as those made using known activator solutions, while being less corrosive, particularly to soft metals such as aluminum. Exemplary anti-corrosive activator solutions may comprise alkaline buffering agent, chelating agent, silicate, water and in some exemplary embodiments, adjunct ingredients.

To enhance biofilm removal and disinfectant efficacy, alkaline in-use disinfectant and/or sanitizer solution may comprise alkaline buffering agents. Alkaline buffering agents may be provided in an anti-corrosive activator solution instead of being provided in a disinfectant/sanitizer cleaner solution. If the alkaline buffering agents were instead added to the disinfectant/sanitizer cleaner solution, degradation of the hydrogen peroxide present therein may occur. Useful alkaline buffering agents may be selected from the group of: sodium carbonate, sodium bicarbonate, potassium carbonate, potassium bicarbonate and combinations thereof. A single alkaline buffering agent or a combination of alkaline buffering agents may be present in anti-corrosive activator solution at a weight percentage of the solution of from about 2% to about 10% or from about 4% to about 6% of total percentage of alkaline buffering agent(s). Some exemplary anti-corrosive activator solutions may comprise a combination of from about 3% to about 8% of sodium carbonate and from about 3% to about 8% of potassium carbonate.

Exemplary anti-corrosive activator solutions may further comprise chelating agent. It has been found that disinfectant/sanitizer cleaner solution may have increased efficacy in "soft" water, for example, water containing low amounts of calcium or no calcium. Moreover, it has been found that relatively high levels of calcium may cause precipitation with alkaline buffering agents. Thus, it may be desirable to include chelating agent in an anti-corrosive activator solution. Useful chelating agent may be selected from the group of: ethylenediaminetetraacetic acid ("EDTA"), EDTA derivatives, 8-hydroxyquinoline, 1 hydroxyethylidene-1,1-diphosphonic acid ("HEDP"), HEDP derivatives, glutamic acid diacetic acid ("GLDA"), GLDA derivatives, diethylenetriaminepentaacetic acid ("DTPA"), DPTA derivatives, N-(2-Hydroxyethyl)ethylenediaminetriacetic acid ("HEDTA"), ethanoldigl ycinic acid ("EDG"), glucoheptonate, sodium pyrophosphate, potassium hypophosphite, sodium tripolyphosphate, citric acid and combinations thereof. A single chelating agent or a combination of chelating agents may be present in anti-corrosive activator solution at a weight percentage of the solution of from about 2% to about 10% or from about 4% to about 6% of total percentage of chelating agent(s). Some exemplary anti-corrosive activator solutions may comprise from about 3% to about 8% of EDTA.

Exemplary anti-corrosive activator solutions may further comprise silicate. As described in further detail below, overall stability, lack of reduction of the disinfectant capacity and anti-corrosive capacity maintenance is demonstrated utilizing silicate according to the present disclosure. The positive outcome is achieved even absent addition of yet other chemical components which would have negatively affected one or more of the desirable properties and increase cost.

A single silicate or combination of silicates may be present in anti-corrosive activator solution such that it results in soluble $SiO_2$ being present in the solution at a weight percentage of at least about 1% of the solution. In some exemplary anti-corrosive activator solutions, the silicate or silicates may be present by weight of the solution, at from about 0.1% to about 1%, from about 0.2% to about 0.8%, from about 0.4% to about 0.5%. It is believed that these levels of silicate may optimize solubility of the silicate, while providing for good corrosion protection.

Exemplary sources of silicate may be selected from the group of sodium silicate, potassium silicate and mixtures thereof. Useful sodium silicates may be selected from the group of: sodium metasilicate pentahydrate (e.g. Metso Pentabead® 20 from PQ Corporation (Valley Forge, Pa.)), anhydrous sodium metasilicate (e.g., Metso Pentabead® 2048 from PQ Corporation (Valley Forge, Pa.)) and combinations thereof. Useful potassium silicates may be selected from the group of: potassium metasilicate, anhydrous potassium metasilicate, potassium silicate solution (e.g., Kasil® 1, Kasil® 33 and/or Kasolv® from PQ Corporation (Valley Forge, Pa.) and combinations thereof. Table 1 shows exemplary ranges of weight percentages of the anti-corrosive activator solution of sources of silicate that result in soluble $SiO_2$ being present in the solution at a weight percentage of at least about 1% of the solution.

TABLE 1

| Silicate Source | Wt % of Silicate Source to provide 0.1% $SiO_2$ in Anticorrosive Activator Solution | Wt % of Silicate Source to provide 1% $SiO_2$ in Anticorrosive Activator Solution |
| --- | --- | --- |
| Sodium metasilicate pentahydrate | 0.35% | 3.5% |

TABLE 1-continued

| Silicate Source | Wt % of Silicate Source to provide 0.1% SiO$_2$ in Anticorrosive Activator Solution | Wt % of Silicate Source to provide 1% SiO$_2$ in Anticorrosive Activator Solution |
|---|---|---|
| Sodium metasilicate anhydrous | 0.22% | 2.2% |
| Kasil 1 (29% potassium silicate solution) | 0.48% | 4.8% |
| Kasil 33 (36% potassium silicate solution) | 0.41% | 4.1% |
| Kasolv (Spray-Dried Hydrous potassium silicate) | 0.19% | 1.9% |

In some exemplary anti-corrosive activator solutions, from about 1.40% to about 1.75% Metso Pentabead 20 is present to provide from about 0.4% to about 0.5% SiO$_2$ in the exemplary anti-corrosive activator solution.

In some exemplary anti-corrosive activator solutions, sodium metasilicate pentahydrate (Na$_2$O.SiO$_2$.5 H$_2$O; e.g. Metso Pentabead 20 from PQ Corporation) may be used as the SiO$_2$ source, for its maximum solubility in alkaline in-use solutions because compared to less alkaline silicates, it has lower hygroscopy upon storage and faster dissolution compared to anhydrous sodium metasilicate, and lower cost compared to potassium silicates.

Adjunct ingredients may be present in anti-corrosive activator solution at any useful weight percentage of the disinfectant solution. Adjunct ingredients may be selected from the group of: dyes (e.g. fluorescent dyes including, but not limited to fluorescein), colorants, antifoam agents, foaming agents, surfactants, thickening agents and combinations thereof.

Once desired components of anti-corrosive activator solution are mixed together, a sufficient quantity of water is added to the bring the solution up to the desired volume.

Anti-corrosive activator solution may have any useful alkaline pH. Exemplary activator solutions may have a pH ranging from about 8 to about 14, from about 10 to about 14 or from about 11 to about 13.

Examples and Data:

In reference to the examples and data set forth below, overall stability, lack of reduction of the disinfectant capacity and anti-corrosive capacity maintenance in conjunction with an approved U.S. FDA GRAS status, and additionally or alternatively also being free from restrictions relating to release in waste water, is demonstrated in alkaline in-use disinfectant and/or sanitizer solutions formulated with silicates according to the present disclosure. A positive outcome may be achieved even absent addition of yet other chemical components which may negatively affect one or more of the desirable properties and/or increase cost.

For the purposes of the examples and data, in-use solutions are characterized as an "in-use disinfectant solution" and "in-use sanitizer solution," although it should be understood that the in-use solutions could function as both a disinfectant and a sanitizer depending upon the microbes that are present on a substrate treated with the in-use solutions and/or the level of microbial kill required.

A disinfectant/sanitizer cleaner solution having the formula set forth in Table 2 is made as follows.

TABLE 2

| Component | Weight Percentage of Solution |
|---|---|
| QAC (Barquat ™ 4250Z from Lonza (Allendale, NJ)) | 6% |
| Hydrogen Peroxide | 6.3% |
| Deionized (DI) Water | qs |

The formula amount of DI water is weighed into an appropriate container, and mild mechanical stirring is provided. The formula amount of hydrogen peroxide, 35% or 50% concentrate, is weighed in a container and added while stirring. The formula amount of QAC is weighed in a container and added while stirring. The resulting pH of the solution is in the range from 4.0 to 6.0.

A known activator solution having the formula set forth in Table 3 is made as follows:

TABLE 3

| Component | Weight Percentage of Solution |
|---|---|
| Potassium Carbonate | 6% |
| Sodium Carbonate | 6% |
| EDTA | 4.9% |
| Deionized (DI) Water | qs |

The formula amount of DI water is weighed into an appropriate container, and mild mechanical stirring is provided. The formula amount of sodium carbonate is weighed in a container and added while stirring. The formula amount of potassium carbonate is weighed in a container and added while stirring. The formula amount of EDTA is weighed out in a container and added while stirring. After dissolution of all components, the resulting pH of the solution is in the range from 11 to 13.5.

An anti-corrosive activator solution having the formula set forth in Table 4 is made as follows:

TABLE 4

| Component | Weight Percentage of Solution |
|---|---|
| Sodium Carbonate | 6% |
| Potassium Carbonate | 6% |
| EDTA | 4.9% |
| Sodium Metasilicate Pentahydrate (Metso Pentabead ® 20 from PQ Corporation) | 1% |
| Deionized (DI) Water | qs |

The formula amount of DI water is weighed into an appropriate container, and mild mechanical stirring is provided. The formula amount of sodium carbonate is weighed in a container and added while stirring. The formula amount of potassium carbonate is weighed in a container and added while stirring. The formula amount of EDTA is weighed out in a container and added while stirring. The formula amount sodium metasilicate pentahydrate is weighed in a container and added while stirring. After dissolution of all components, the resulting pH of the solution is in the range from 11 to 13.5.

Comparative Alkaline in-use Disinfectant Solution:

A comparative alkaline in-use disinfectant solution is made by mixing the disinfectant/sanitizer cleaner solution of Table 2, the known activator solution of Table 3 and water at a v/v/v ratio of 1:1:10. The required amount of diluent water is measured into an appropriate container first. The diluent can be DI water for lab testing, but can also be tap, 'city', or 'well' water. The required amounts of disinfectant solution and anti-corrosive activator solution are added to the diluent in any order. The pH of the resulting alkaline in-use disinfectant solution is 11.

Exemplary Alkaline in-use Disinfectant Solution:

An alkaline in-use disinfectant solution according to the present disclosure is made by mixing the disinfectant/sanitizer cleaner solution of Table 2, the anti-corrosive activator solution of Table 4 and water at a v/v/v ratio of 1:1:10. The required amount of diluent water is measured into an appropriate container first. The diluent can be DI water for lab testing, but can also be tap, 'city', or 'well' water. The required amounts of disinfectant solution and anti-corrosive activator solution are added to the diluent in any order. The pH of the resulting alkaline in-use disinfectant solution is 11.

Comparative Alkaline in-use Sanitizer Solution:

A comparative alkaline in-use sanitizer solution is made by mixing the disinfectant/sanitizer cleaner solution of Table 2, the known activator solution of Table 3 and water at a v/v/v ratio of 1:1:64. The required amount of diluent water is measured into an appropriate container first. The diluent can be DI water for lab testing, but can also be tap, 'city', or 'well' water. The required amounts of Disinfectant Solution and Activator Solution are added to the diluent in any order. The pH of the resulting alkaline in-use sanitizer solution is 11.

Exemplary Alkaline in-Use Sanitizer Solution:

An alkaline in-use sanitizer solution according to the present disclosure is made by mixing the disinfectant/sanitizer cleaner solution of Table 2, the anti-corrosive activator solution of Table 4 and water at a v/v/v ratio of 1:1:64. The required amount of diluent water is measured into an appropriate container first. The diluent can be DI water for lab testing, but can also be tap, 'city', or 'well' water. The required amounts of disinfectant solution and anti-corrosive activator solution are added to the diluent in any order. The pH of the resulting alkaline in-use disinfectant solution is 11.

Anti-corrosiveness of the comparative and exemplary alkaline in-use disinfectant and/or sanitizer solutions are measured by immersing test substrates therein. Testing on metal substrates and plastic substrates is undertaken as described below.

Metal Substrates:

Anti-corrosiveness of the comparative and exemplary alkaline in-use disinfectant and/or sanitizer solutions are measured by immersing metal coupons identified in Table 5 in the solutions. Aluminum 1100, 3003 5052 are grades of aluminum that are typically used to make heat exchanger coils.

TABLE 5

| Sample # | Material | Supplier | Item # | Dimensions (inches) |
|---|---|---|---|---|
| 1 | Aluminum 1100 | ACT Test Panel | 59575 | 0.030 × 1 × 3 |
| 2 | Aluminum 5052 | ACT Test Panel[1] | 59298 | 0.025 × 1 × 4 |
| 3 | Aluminum 3003 | ACT Test Panel[1] | 20955 | 0.063 × 1 × 4 |
| 4 | Aluminum 7075 | ACT Test Panel[1] | 34782 | 0.032 × 1 × 4 |
| 5 | Copper | Alabama Specialty[2] | CO1004190104000 | 0.063 × 0.5 × 3 |
| 6 | Brass | Alabama Specialty[2] | CO10044320104000 | 0.125 × 0.5 × 3 |
| 7 | Bronze | Alabama Specialty[2] | CO100440010400 | 0.063 × 0.5 × 3 |
| 8 | Cold Rolled Carbon Steel | ACT Test Panel[1] | 17914 | 0.032 × 1 × 4 |
| 9 | Hot Dipped Galvanized Steel | ACT Test Panel[1] | 31895 | 0.030 × 1 × 4 |
| 10 | Stainless Steel 304 | ACT Test Panel[1] | 56131 | 0.030 × 1 × 3 |
| 11 | Stainless Steel 316 | ACT Test Panel[1] | 58943 | 0.030 × 1 × 4 |

[1]ACT Test Panels LLC, 273 Industrial Drive, Hillsdale, MI 49242
[2]Alabama Specialty Products, Inc., 152 Metal Samples Road, Munford, AL 36268

Prior to being immersed, each metal coupon is cleaned in Liquinox® Detergent from Alconox (White Plains, N.J.), rinsed with DI water followed by isopropyl alcohol. After air-drying, each coupon is weighed on an analytical balance. One sample of each metal coupon is left untreated, two samples are immersed in DI water and two samples of each metal coupon are immersed in one of the alkaline in-use disinfectant and sanitizer solutions as described below for a consecutive period of ten days (240 hours), which is believed to correspond to a surface being subjected to treatment with alkaline in-use disinfectant and/or sanitizer solution for 10 consecutive minutes per day, every day for 5.5 years, or to correspond to a surface being treated with alkaline in-use disinfectant solution for a consecutive period of 10 minutes per week, every week, for 27.5 years. Over the ten-day immersion test period, the alkaline in-use solutions are replaced after 3 days and after 7 days with freshly-prepared alkaline in-use solutions. After treatment, metal coupons are rinsed with DI water followed by being rinsed with isopropyl alcohol. After air-drying, each metal coupon is photographed and weighed on an analytical balance.

Figure 1:
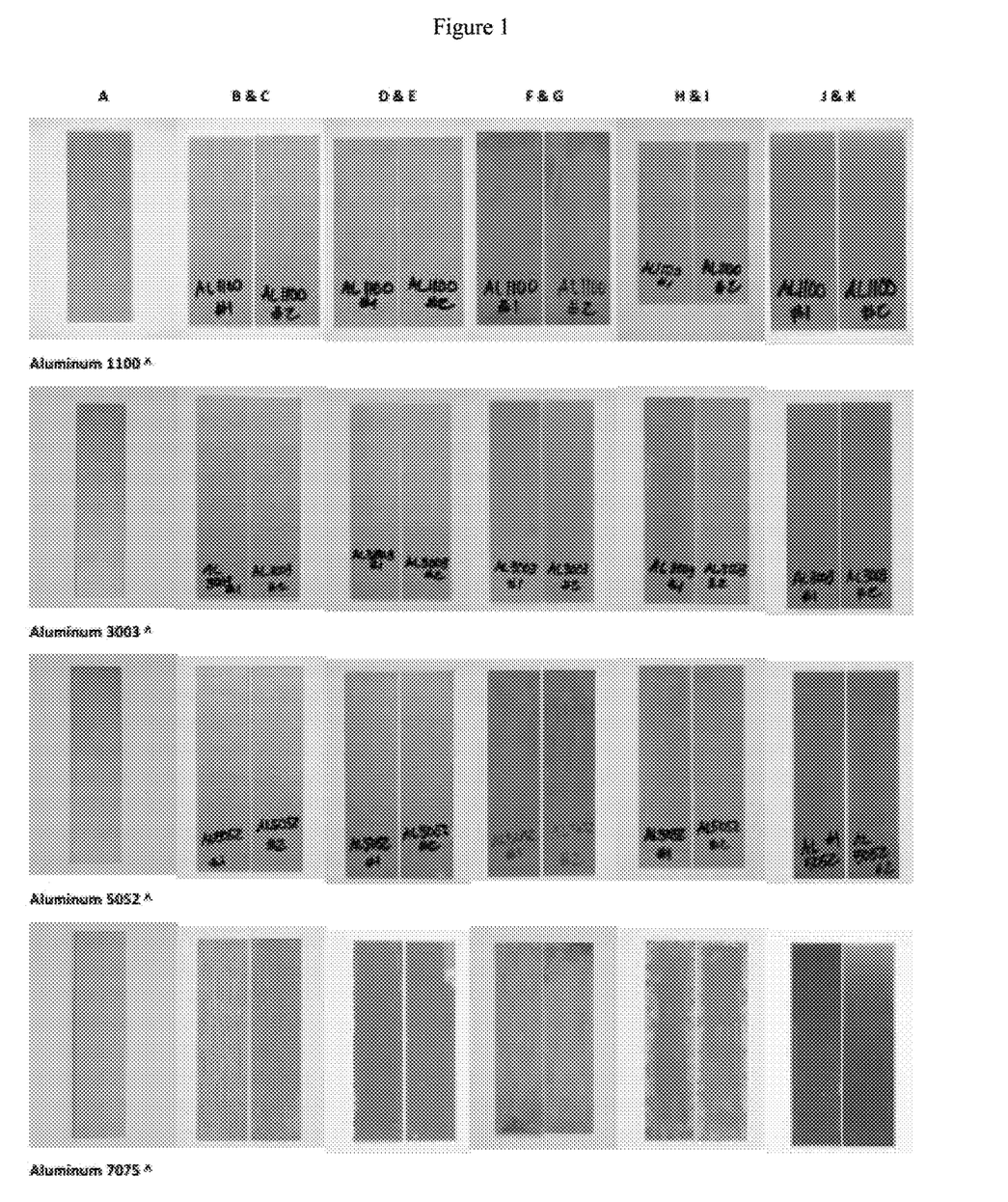
FIG. 1 contains photos of different grades of aluminum that are untreated and treated with alkaline disinfectant and sanitizer solutions.
Figure 2:
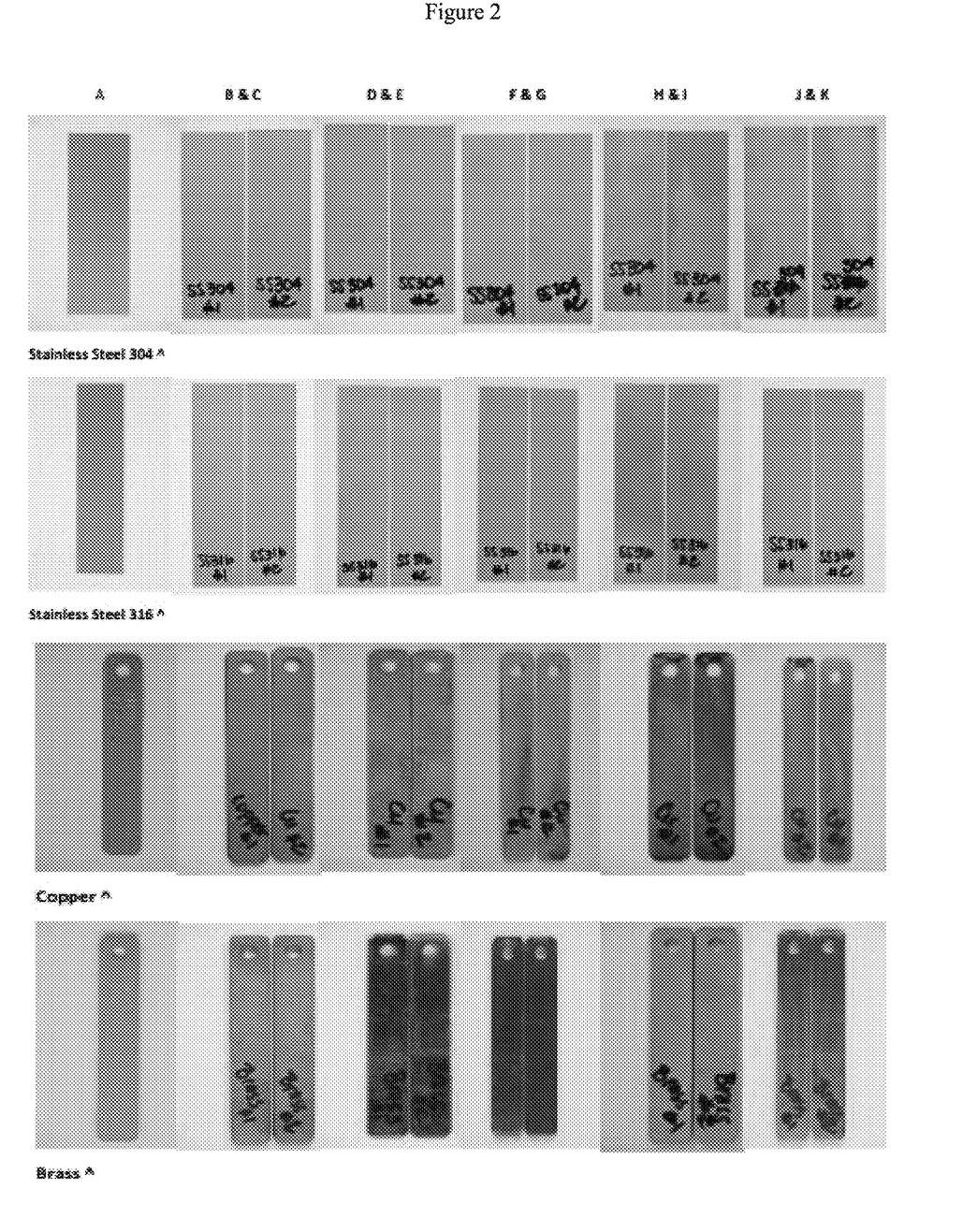
FIG. 2 contains photos of copper, brass and different grades of stainless steel that are untreated and treated with alkaline disinfectant and sanitizer solutions.
Figure 3:
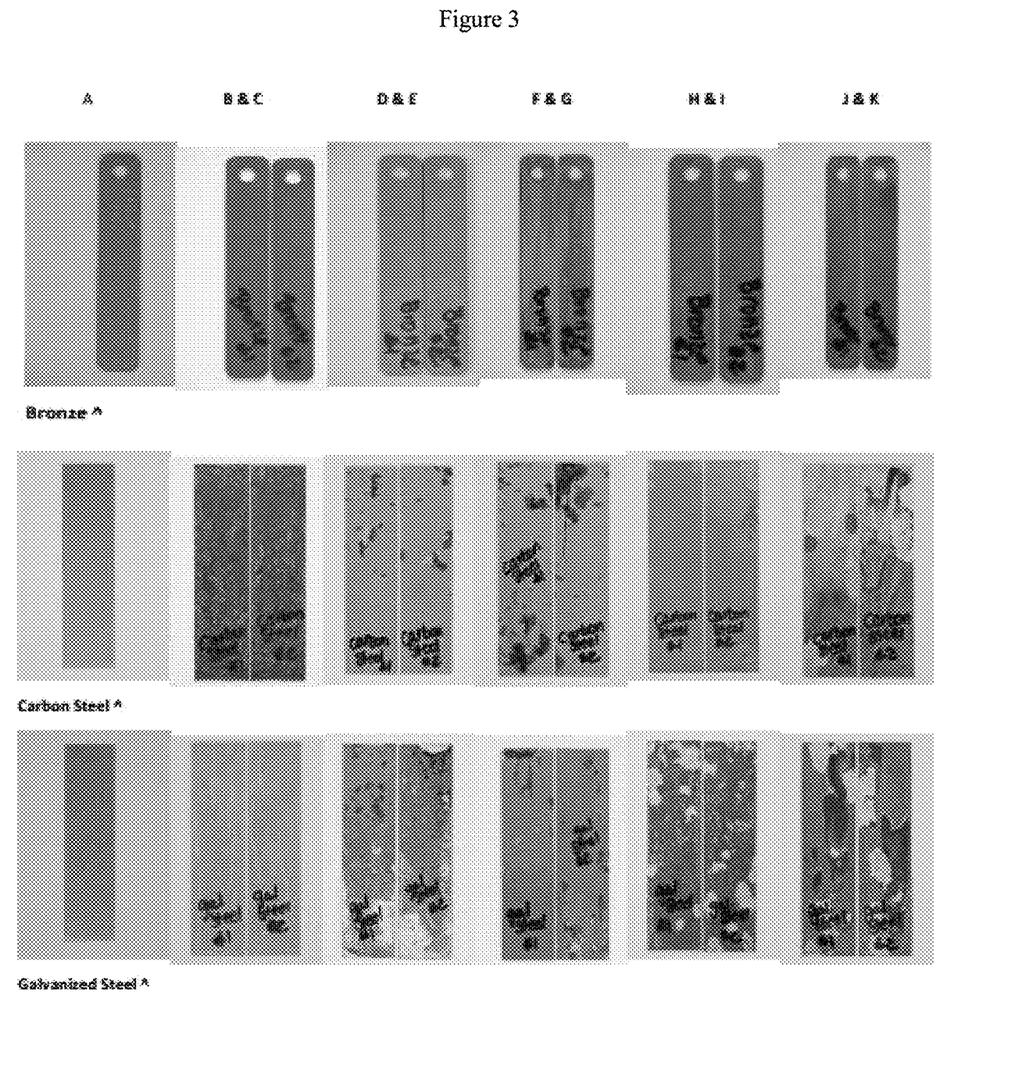
FIG. 3 contains photos of bronze, carbon steel and galvanized steel that are untreated and treated with alkaline disinfectant and sanitizer solutions.

Photos of the each of the metal coupons tested are shown in FIGS. 1-3. For example, referencing the first row of photos in FIG. 1, metal coupons of Aluminum 1100 are shown. Moving left to right, sample "A" is the untreated coupon, samples "B" and "C" are the coupons that are immersed in water, samples "D" and "E" are the coupons immersed in exemplary alkaline in-use disinfectant solution, samples "F" and "G" are the coupons immersed in comparative alkaline in-use disinfectant solution, samples "H" and "I" are the coupons immersed in exemplary alkaline in-use sanitizer solution and samples "J" and "K" are the coupons immersed in comparative sanitizer solution. Referencing the second row of photos, metal coupons of Aluminum 3003 are shown and so on.

A percentage of change in mass experienced by a metal coupon after being immersed in water or an alkaline in-use composition and over the ten-day test period is calculated and set forth in Table 6 below:

TABLE 6

| Sample # | Material | DI Water | Comparative In-Use Disinfectant Solution (g) | Exemplary In-Use Disinfectant Solution (g) | Comparative In-Use Sanitizer Solution (g) | Exemplary In-Use Sanitizer Solution (g) |
|---|---|---|---|---|---|---|
| 1 | Aluminum 1100 | 0.010 | −5.40 | −2.19 | 0.013 | 0.056 |
| 2 | Aluminum 5052 | 0.015 | −7.82 | −3.53 | 0.001 | 0.026 |
| 3 | Aluminum 3003 | 0.003 | −2.23 | −0.82 | 0.013 | 0.025 |
| 4 | Aluminum 7075 | 1.24 | −4.16 | −1.88 | 0.32 | −0.93 |
| 5 | Copper | −0.005 | −0.90 | −0.53 | −0.71 | −0.52 |
| 6 | Brass | −0.003 | −0.70 | −0.22 | −0.56 | −0.19 |
| 7 | Bronze | 0.024 | −1.64 | −0.42 | −0.004 | −0.064 |
| 8 | Cold Rolled Carbon Steel | −0.14 | −0.15 | −2.54 | 0.070 | −0.81 |
| 9 | Hot Dipped Galvanized Steel | 0.019 | −2.48 | −3.89 | −1.89 | −2.97 |
| 10 | Stainless Steel 304 | 0.000 | −0.005 | 0.001 | −0.001 | 0.005 |
| 11 | Stainless Steel 316 | 0.001 | −0.005 | −0.001 | 0.001 | 0.003 |

Upon visual inspection of the photos in FIGS. 1-3 and data derived from immersion testing, the following may be surmised. Alkaline in-use disinfectant and/or sanitizer solutions comprising anti-corrosive activator solution, protect well against corrosion of aluminum 1100, 3003 and 5052 grades, with minimal corrosion and no loss in mass after ten days submerged in exemplary alkaline in-use disinfectant solution (equivalent to 5.5 years of daily disinfection, or 27 years of weekly disinfection). While the quantitative data appears to show that alkaline in-use disinfectant and/or sanitizer solution comprising anti-corrosive activator solution protects Al 7075 from corrosive effects, minor corrosion is visibly evident, even though not obvious, in FIG. 1. By contrast, the comparative alkaline in-use disinfectant solution (without silicate), at disinfection dilution, caused up to about an 8% loss of the mass of aluminum samples after 10 days of immersion. Carbon steel shows minor corrosion, and stainless steel shows no corrosion, upon treatment with the exemplary alkaline in-use disinfectant and/or sanitizer solutions according to the present disclosure. The exemplary alkaline in-use disinfectant and/or sanitizer solutions are compatible with 304 stainless steel, 316 stainless steel, copper, and brass, yet, they are only semi-compatible with cold-rolled carbon steel. Similar testing of cast iron shows that the exemplary alkaline in-use disinfectant and/or sanitizer solutions are not compatible with cast iron.

Plastic Substrates:

The same methodology for measuring and quantifying anti-corrosiveness of the comparative and exemplary alkaline in-use disinfectant and/or sanitizer solutions on metal substrates is used to test plastic substrates. A percentage of change in mass experienced by plastic coupons after being immersed in water or an alkaline in-use composition and over the ten-day test period is calculated and set forth in Table 7 below:

TABLE 7

| Sample # | Material | Comparative Alkaline in-use Disinfectant Solution (g) | Exemplary Alkaline in-use Disinfectant Solution (g) | Comparative Alkaline in-use Sanitizer Solution (g) | Exemplary Alkaline in-use Sanitizer Solution (g) |
|---|---|---|---|---|---|
| 12 | High Density Polyethylene | 0.10 | 0.12 | 0.09 | 0.16 |
| 13 | Low Density Polyethylene | 0.15 | 0.14 | 0.15 | 0.16 |
| 14 | Polypropylene | 0.06 | 0.06 | 0.12 | 0.23 |
| 15 | Polyvinylchloride | 0.13 | 0.13 | 0.12 | 0.16 |
| 16 | Polytetrafluoroethylene | 0.01 | 0.01 | 0.02 | 0.03 |
| 17 | Polyoxymethylene | 0.48 | 0.48 | 0.49 | 0.51 |
| 18 | Lexan ™ (Polycarbonate) | −7.08 | −12.02 | −0.92 | −1.25 |
| 19 | Makrolon ™ (Polycarbonate) | −7.55 | −4.97 | −1.74 | −1.52 |

With the exception of the polycarbonate coupons, no appreciable changes in mass are observed in the plastic coupons after being immersed in water.

Based upon the data derived from immersion testing, the following may be surmised. Exemplary alkaline in-use disinfectant and/or sanitizer solutions comprising anti-corrosive activator solution, perform similarly to the known alkaline in-use solutions (without silicates) when applied to these plastics. As a result, it is believed that adding silicate to in-use solutions does not change compatibility of the in-use solutions with these plastics. Like the known alkaline in-use formulas (without silicates), exemplary alkaline in-use disinfectant and/or sanitizer solutions may not be compatible with polycarbonates.

Similar testing of various synthetic rubbers shows that the exemplary alkaline in-use disinfectant and/or sanitizer solutions do not negatively affect those materials.

The anti-corrosive activator solution described above may be analyzed to determine whether silicates will precipitate out of solution during long-term storage. First, a small amount of precipitate is observed in a first sample of the anti-corrosive activator solution after 12 months of storage at room temperature or 40° C. Second, a small amount of precipitation is seen in anti-corrosive activator solution after three freeze-thaw cycles, wherein each cycle consists of 24 hours in a freezer set at approximately 10° C., 24 hours at room temperature and 24 hours at 40° C. Thus, not only are silicates surprisingly soluble in anti-corrosive activator solutions, they remain substantially soluble over time.

Anti-corrosiveness of alkaline in-use disinfectant and/or sanitizer solutions comprising anti-corrosive activator solution subjected to the aging tests above are measured via the ten-day immersion test described above. No performance loss is observed.

Analysis of silicates by induction-coupled spectroscopy (ICP) on an anti-corrosive activator solution sample aged over 16 months indicated precipitation loss of about 5%. The result is based on filtering the aged solution containing precipitate, ICP analysis for Si in the filtrate, and comparison to data for a fresh solution without precipitate. However, the anti-corrosive activity of the solution does not lose corrosion inhibition under these conditions, as demonstrated via the ten-day immersion test described above.

As described above, the overall stability, lack of reduction of the disinfectant capacity, anti-corrosive capacity maintenance was demonstrated with silicates in the absence of the other chemical components which would have negatively affected one or more of the desirable properties and increased cost.

Efficacy of in-use disinfectant solution on a hard surface is tested using the AOAC Use-Dilution Method, AOAC Method No. 955.14; 955.15; 964.02, which is incorporated by reference herein, as is required by the U.S. Environmental Protection Agency ("the EPA"). In brief, the test is conducted as follows.

An alkaline in-use disinfectant solution according to the present disclosure (referred to in Table 8 below as the "comparative solution") is made by mixing the disinfectant/sanitizer cleaner solution of Table 2, the known activator solution of Table 3 and sterile tap water at a v/v/v ratio of 1:1:10.

An alkaline in-use disinfectant solution according to the present disclosure (referred to in Table 8 below as the "exemplary solution") is made by mixing the disinfectant/sanitizer cleaner solution of Table 2, the anti-corrosive activator solution of Table 4 and sterile tap water at a v/v/v ratio of 1:1:10.

Test organisms include *Pseudomonas aeruginosa* (ATCC 15442), *Salmonella enterica* (ATCC 10708) and *Staphylococcus aureus* (ATCC 6538). Each of the test organisms is grown in a liquid culture medium containing 5% fetal bovine serum as the artificial soil load, resulting in a test culture. Sterilized carriers are inoculated with a volume of the test culture. Inoculated slides (i.e., "carriers") are completely dried in an incubator. Test carriers are treated with the alkaline in-use disinfectant solution and incubated for 9 minutes at 20±1° C. Control carriers are treated with a buffered saline solution and are allowed to sit for 9 minutes at 20±1° C.

At the conclusion of the contact time, test and control carriers are chemically neutralized in neutralizing subculture medium (Letheen Broth+0.14% Lecithin+1.0% Tween 80+0.1% Sodium Thiosulfate+0.01% Catalase). Neutralized test substances are visually examined for growth.

The effect of the alkaline in-use disinfectant solutions and the effect of the buffered saline solution (study control) on the test substrate is tested in triplicate (n=3), and the results are set forth in Table 8 below:

TABLE 8

| Sample ID | Test Organism | In-Use Disinfectant Solution | Number of Carriers Exposed | Showing Growth | Confirmed As Test Organism |
|---|---|---|---|---|---|
| 1A | *Pseudomonas aeruginosa* (ATCC 15442) | Exemplary Solution | 60 | 2 | 2 |
| 1B | *Salmonella enterica* (ATCC 10708) | | 60 | 0 | 0 |
| 1C | *Staphylococcus aureus* (ATCC 6538) | | 60 | 1 | 1 |
| 1D | *Pseudomonas aeruginosa* (ATCC 15442) | Comparative Solution | 60 | 1 | 1 |
| 1E | *Salmonella enterica* (ATCC 10708) | | 60 | 0 | 0 |
| 1F | *Staphylococcus aureus* (ATCC 6538) | | 60 | 0 | 0 |
| 2A | *Pseudomonas aeruginosa* (ATCC 15442) | Exemplary Solution | 60 | 1 | 1 |
| 2B | *Salmonella enterica* (ATCC 10708) | | 60 | 0 | 0 |
| 2C | *Staphylococcus aureus* (ATCC 6538) | | 60 | 2 | 2 |
| 2D | *Pseudomonas aeruginosa* (ATCC 15442) | Comparative Solution | 60 | 1 | 1 |
| 2E | *Salmonella enterica* (ATCC 10708) | Comparative Solution | 60 | 0 | 0 |
| 2F | *Staphylococcus aureus* (ATCC 6538) | Comparative Solution | 60 | 0 | 0 |
| 3A | *Pseudomonas aeruginosa* (ATCC 15442) | Exemplary Solution | 60 | 0 | 0 |
| 3B | *Salmonella enterica* (ATCC 10708) | Exemplary Solution | 60 | 1 | 1 |
| 3C | *Staphylococcus aureus* (ATCC 6538) | Exemplary Solution | 60 | 0 | 0 |
| 3D | *Pseudomonas aeruginosa* (ATCC 15442) | Comparative Solution | 60 | 0 | 0 |
| 3E | *Salmonella enterica* (ATCC 10708) | Comparative Solution | 60 | 0 | 0 |
| 3F | *Staphylococcus aureus* (ATCC 6538) | Comparative Solution | 60 | 1 | 1 |

Per the EPA, for a carrier to be deemed disinfected, the efficacy performance requirements for label claims state that the test substance must meet the following criteria with respect to each microorganism. For *Staphylococcus aureus*, these microorganisms must be killed (i.e., show no growth) on 57 out of the 60 inoculated carriers. For *Pseudomonas aeruginosa*, these microorganisms must be killed on 54 out of the 60 inoculated carriers. For *Salmonella enterica*, these microorganisms must be killed on 59 out of the 60 inoculated carriers. The study controls are found to pass all performance criteria detailed in the study controls description section of the method.

As can be seen in Table 8, and in-use disinfectant solution comprising silicate according to the present disclosure has the similar disinfectant properties as a disinfectant solution without silicate. Thus, it may be surmised that the presence of silicate does not negatively impact efficacy of in-use disinfectant solution according to the present disclosure.

Efficacy of in-use sanitizer solution is tested on a hard, inanimate, non-porous, non-food contact surface using ASTM, E1153, which is incorporated by reference herein. This method is in compliance with the requirements of the U.S. Environmental Protection Agency (EPA). In brief, the test is conducted as follows.

An alkaline in-use sanitizer solution according to the present disclosure (referred to in Table 9 below as the "comparative solution") is made by mixing the disinfectant/sanitizer cleaner solution of Table 2, the known activator solution of Table 3 and sterile tap water at a v/v/v ratio of 1:1:64.

An alkaline in-use sanitizer solution according to the present disclosure (referred to in Table 9 below as the "exemplary solution") is made by mixing the disinfectant/sanitizer cleaner solution of Table 2, the anti-corrosive activator solution of Table 4 and sterile tap water at a v/v/v ratio of 1:1:64.

The test organisms are *Enterobacter aerogenes* (ATCC 13048) and *Staphylococcus aureus* (ATCC 6538). The test organism is grown in a liquid culture medium containing 5% fetal bovine serum as the artificial soil load, resulting in a test culture. Sterilized slides (i.e., "carriers") are inoculated with a volume of the test culture. Inoculated slides are completely dried in an incubator. Test carriers are treated with the comparative and exemplary alkaline in-use sanitizer solutions and incubated for a 2.5 minute exposure time at room temperature (21° C.). Control carriers are treated with a buffered saline solution and are allowed to sit for the same contact time as test carriers. At the conclusion of the contact time, test and control carriers are chemically neutralized in Letheen Broth+0.28% Lecithin+1.0% Tween 80+0.1% Sodium Thiosulfate+0.01% Catalase for 30 minutes. Dilutions of the neutralized test substance are evaluated using appropriate growth media to determine the surviving microorganisms at the respective contact time. The effect of the test substance is compared to the effect of the control substance in order to determine microbial reductions.

The efficacy performance requirements for label claims state that the test substance must demonstrate a minimum 99.9% reduction of test survivors as compared to the population control to be considered an effective non-food contact sanitizer. The study controls must perform according to the criteria detailed in the study controls description section.

The effect of the alkaline in-use sanitizer solutions and the effect of the buffered saline solution (study control) on the test substrate is tested in triplicate (n=3), and the results are set forth in Table 9 below:

TABLE 9

| Sample ID | Test Organism | In-Use Sanitizer Solution | Average $\text{Log}_{10}$ CFU/ Carrier | Geometric Mean CFU/ Carrier | Percent Reduction |
|---|---|---|---|---|---|
| 1A | *Enterobacter aerogenes* (ATCC 13048) | Exemplary Solution | <1.4 | $<2.51 \times 10^1$ | >99.9% |
| 1B | *Staphylococcus aureus* (ATCC 6538) | | <2.4 | $<2.51 \times 10^2$ | >99.9% |
| 1C | *Enterobacter aerogenes* (ATCC 13048) | Comparative Solution | <1.4 | $<2.51 \times 10^1$ | >99.9% |
| 1D | *Staphylococcus aureus* (ATCC 6538) | | <1.4 | $<2.51 \times 10^1$ | >99.9% |
| 2A | *Enterobacter aerogenes* (ATCC 13048) | Exemplary Solution | <1.4 | $<2.51 \times 10^1$ | >99.9% |
| 2B | *Staphylococcus aureus* (ATCC 6538) | | <2.4 | $<2.51 \times 10^2$ | >99.9% |
| 2C | *Enterobacter aerogenes* (ATCC 13048) | Comparative Solution | <1.4 | $<2.51 \times 10^1$ | >99.9% |
| 2D | *Staphylococcus aureus* (ATCC 6538) | | <1.4 | $<2.51 \times 10^1$ | >99.9% |
| 3A | *Enterobacter aerogenes* (ATCC 13048) | Exemplary Solution | <1.4 | $<2.51 \times 10^1$ | >99.9% |
| 3B | *Staphylococcus aureus* (ATCC 6538) | | <2.4 | $<2.51 \times 10^2$ | >99.9% |
| 3C | *Enterobacter aerogenes* (ATCC 13048) | Comparative Solution | <1.4 | $<2.51 \times 10^1$ | >99.9% |
| 3D | *Staphylococcus aureus* (ATCC 6538) | | <1.4 | $<2.51 \times 10^1$ | >99.9% |

CFU = Colony Forming Units
A value of <1 was used in place of zero for calculation purposes.

Under the conditions of this test, an alkaline in-use sanitizer solution according to the present disclosure demonstrated efficacy against *Enterobacter aerogenes* as required by the U.S. EPA following a 2.5 minute exposure time at room temperature (21° C.). Under the conditions of this investigation, an alkaline in-use sanitizer solution according to the present disclosure demonstrated efficacy against *Staphylococcus aureus* as required by the U.S. EPA following a 2.5 minute exposure time at room temperature (21° C.). The study controls are found to pass all performance criteria detailed in the study controls description section of the method.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and figures.

We claim:

1. A two-part alkaline disinfectant and/or sanitizer system consisting of:
    (a) an aqueous disinfectant/sanitizer cleaner solution consisting of quaternary ammonium compound and hydrogen peroxide; and
    (b) an aqueous activator solution consisting of alkaline buffering agent, chelating agent and soluble silicon dioxide, wherein the soluble silicon dioxide is present in the activator solution at a weight percentage of the solution of from about 0.1% to about 1% and wherein the pH of the activator solution is from about 8 to about 14; wherein an in-use disinfectant and/or sanitizer solution consisting of a mixture of the disinfectant/sanitizer cleaner solution and the activator solution has no loss of disinfectant efficacy and/or sanitizer efficacy when compared to an in-use solution comprising the same components minus soluble silicon dioxide.

2. The two-part disinfectant and/or sanitizing system of claim 1, wherein the disinfectant/sanitizer cleaner solution and the activator solution are mixed together in a ratio of about 1:1 (v/v), to form the alkaline in-use solution.

3. The two-part disinfectant and/or sanitizing system of claim 1, wherein the disinfectant/sanitizer cleaner solution, activator solution and water are mixed together at a ratio of from about 1:1:1 to about 1:1:20 (v/v/v), to form the alkaline in-use solution.

4. The two-part disinfectant and/or sanitizing system of claim 1, wherein the disinfectant/sanitizer cleaner solution, activator solution and water are mixed together at a ratio of from about 1:1:64 to about 1:1:128 (v/v/v), to form the alkaline in-use solution.

5. The two-part disinfectant and/or sanitizing system of claim 1, wherein a source of the soluble silicon dioxide in the activator solution is selected from the group of: sodium silicate, potassium silicate and combinations thereof.

6. The two-part disinfectant and/or sanitizing system of claim 5, wherein the potassium silicate is selected from the group of: potassium metasilicate, anhydrous potassium metasilicate, potassium silicate solution, spray-dried hydrous potassium silicate and combinations thereof.

7. The two-part disinfectant and/or sanitizing system of claim 5, wherein the source of the sodium silicate is selected from the group of: sodium metasilicate pentahydrate, anhydrous sodium metasilicate and combinations thereof.

8. The two-part disinfectant and/or sanitizing system of claim 7, wherein the source of the sodium silicate is sodium metasilicate pentahydrate and is present in the activator solution at a weight percentage of the solution of from about 0.35% to about 3.5%.

9. The two-part disinfectant and/or sanitizing system of claim 7, wherein the sodium silicate is anhydrous sodium metasilicate and is present in the activator solution at a weight percentage of the solution of from about 0.22% to about 2.2%.

10. A two-part alkaline disinfectant and/or sanitizer system consisting of:
    (a) a disinfectant/sanitizer cleaner solution consisting of quaternary ammonium compound and hydrogen peroxide; and
    (b) an activator solution consisting of by weight percentage of the activator solution:
        1. from about 3% to about 8% sodium carbonate;
        2. from about 3% to about 8% potassium carbonate;
        3. from about 3% to about 8% ethylenediaminetetraacetic acid; and
        4. from about 0.1% to about 1% $SiO_2$;
wherein the disinfectant/sanitizer cleaner solution and the activator solution are mixed together to form an alkaline in-use solution.

11. A method of disinfecting and/or sanitizing a substrate, the method comprising the steps of:
    (a) forming an alkaline in-use solution by combining:
        1. an aqueous disinfectant/sanitizer cleaner solution consisting of quaternary ammonium compound and hydrogen peroxide; and
        2. an aqueous activator solution consisting of alkaline buffering agent, chelating agent and soluble silicon dioxide, wherein the soluble silicon dioxide is present in the activator solution at a weight percentage of the solution of from about 0.1% to about 1% and wherein the pH of the activator solution is from about 8 to about 14; and
    (b) applying the in-use solution to the substrate.

12. The method of claim 11, comprising making the disinfectant/sanitizer cleaner solution by mixing a powder consisting of quaternary ammonium compound and hydrogen peroxide source with water.

* * * * *

UNITED STATES PATENT AND TRADEMARK OFFICE
CERTIFICATE OF CORRECTION

PATENT NO. : 10,525,157 B2
APPLICATION NO. : 15/664122
DATED : January 7, 2020
INVENTOR(S) : Edward Fu et al.

Page 1 of 1

It is certified that error appears in the above-identified patent and that said Letters Patent is hereby corrected as shown below:

In the Specification

Column 4, Lines 22-23 reads "...bis-quatemary ammonium salts..."; which should be deleted and replaced with "...bis-quaternary ammonium salts..."

Column 8, Line 12 reads "...ethanoldigl ycinic acid ("EDG")..."; which should be deleted and replaced with "...ethanoldiglycinic acid ("EDG")..."

Signed and Sealed this
Third Day of March, 2020

Andrei Iancu
*Director of the United States Patent and Trademark Office*